US011937776B2

United States Patent
Deyanov

(10) Patent No.: US 11,937,776 B2
(45) Date of Patent: Mar. 26, 2024

(54) ADAPTER FOR A MULTI-STAGE CONSOLE CONNECTOR

(71) Applicant: Intuitive Surgical Operations, Inc., Sunnyvale, CA (US)

(72) Inventor: Rumen Deyanov, Fremont, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 488 days.

(21) Appl. No.: 17/057,047

(22) PCT Filed: Jun. 26, 2019

(86) PCT No.: PCT/US2019/039347
§ 371 (c)(1),
(2) Date: Nov. 19, 2020

(87) PCT Pub. No.: WO2020/006147
PCT Pub. Date: Jan. 2, 2020

(65) Prior Publication Data
US 2021/0093168 A1 Apr. 1, 2021

Related U.S. Application Data

(60) Provisional application No. 62/691,453, filed on Jun. 28, 2018.

(51) Int. Cl.
*A61B 1/00* (2006.01)
(52) U.S. Cl.
CPC ...... *A61B 1/00126* (2013.01); *A61B 1/00117* (2013.01); *A61B 1/00124* (2013.01); *A61B 1/00165* (2013.01)

(58) Field of Classification Search
CPC ............ A61B 1/00126; A61B 1/00117; A61B 1/00124; A61B 1/00165; A61B 1/00112;
(Continued)

(56) References Cited

U.S. PATENT DOCUMENTS 4,919,621 A * 4/1990 Ams ................... G02B 6/3817
439/924.1
5,830,124 A * 11/1998 Suzuki ............... A61B 1/00124
600/134
(Continued)

FOREIGN PATENT DOCUMENTS

EP 0928978 A1 7/1999
WO WO-2015142787 A1 * 9/2015 ......... A61B 1/00112

OTHER PUBLICATIONS

International Search Report and Written Opinion for Application No. PCT/US2019/039347, dated Oct. 11, 2019, 11 pages (ISRG12810/PCT).
(Continued)

*Primary Examiner* — Timothy J Neal
*Assistant Examiner* — James Edward Boice

(57) ABSTRACT

A medical device includes an instrument connector. The instrument connector includes a main body and a coupler fixedly attached to the mail body. The main body includes a first interface for a first operational channel for the medical device. The coupler is configured to receive a portion of a cable assembly including a second interface for a second operational channel for the medical device.

15 Claims, 14 Drawing Sheets

(58) Field of Classification Search
CPC ............ A61B 1/00121; A61B 1/00128; A61B 1/00066; A61B 1/0011; A61B 1/00114; A61B 1/00119; A61B 2018/00172; A61B 2017/00477; G02B 6/26; G02B 6/36; G02B 6/3817; G02B 23/24; B02B 6/3825; H01B 11/22
USPC ................ 600/104, 106, 123, 153, 132, 174
See application file for complete search history.

(56) References Cited

U.S. PATENT DOCUMENTS

| | | |
|---|---|---|
| 2004/0266257 A1 | 12/2004 | Ries et al. |
| 2006/0030753 A1* | 2/2006 | Boutillette ......... A61B 1/00135 600/153 |
| 2009/0171147 A1* | 7/2009 | Lee ....................... A61B 17/29 600/137 |
| 2014/0309683 A1* | 10/2014 | Bagwell ............. A61B 18/1492 606/207 |
| 2016/0089000 A1* | 3/2016 | Hara .................. A61B 1/00112 600/112 |
| 2017/0112589 A1* | 4/2017 | Ramkhelawan ....... A61B 1/122 |
| 2017/0181609 A1 | 6/2017 | Tanii |
| 2018/0031775 A1 | 2/2018 | Gurreri et al. |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/2019/039347, dated Jan. 7, 2021, 7 pages.

* cited by examiner

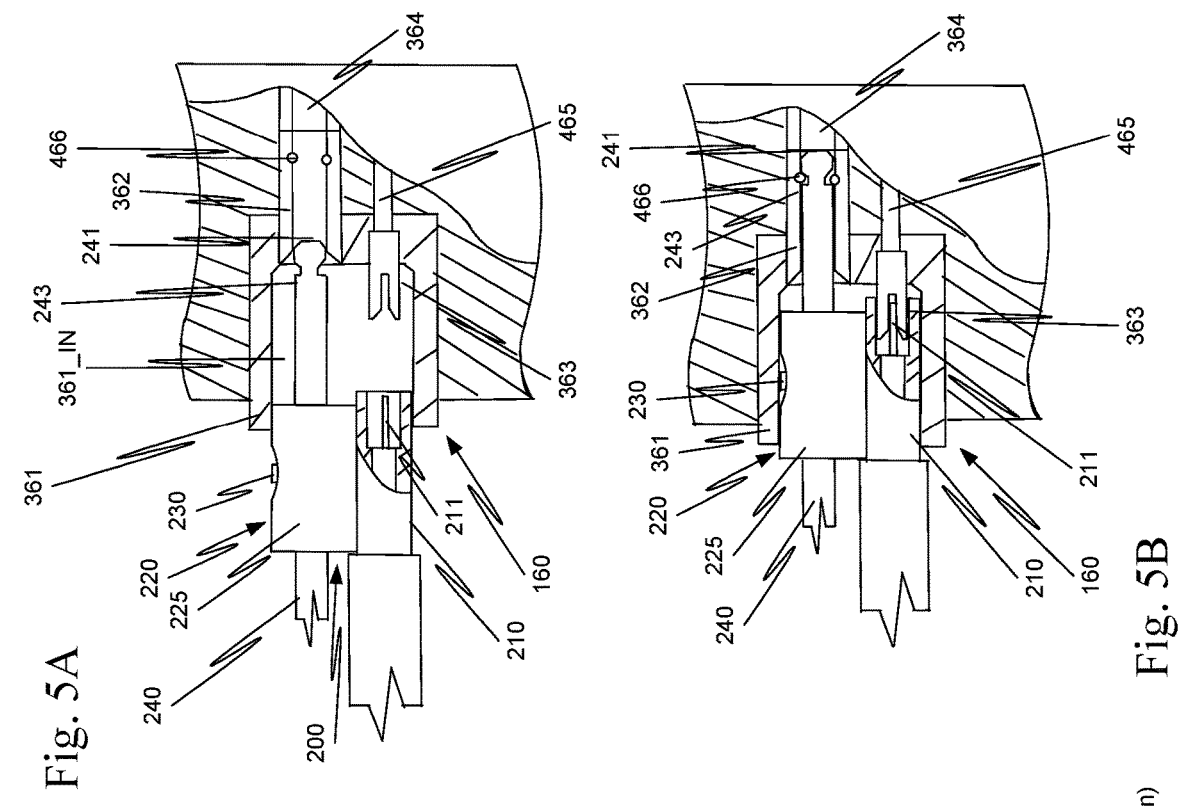
Fig. 4A
Fig. 4B
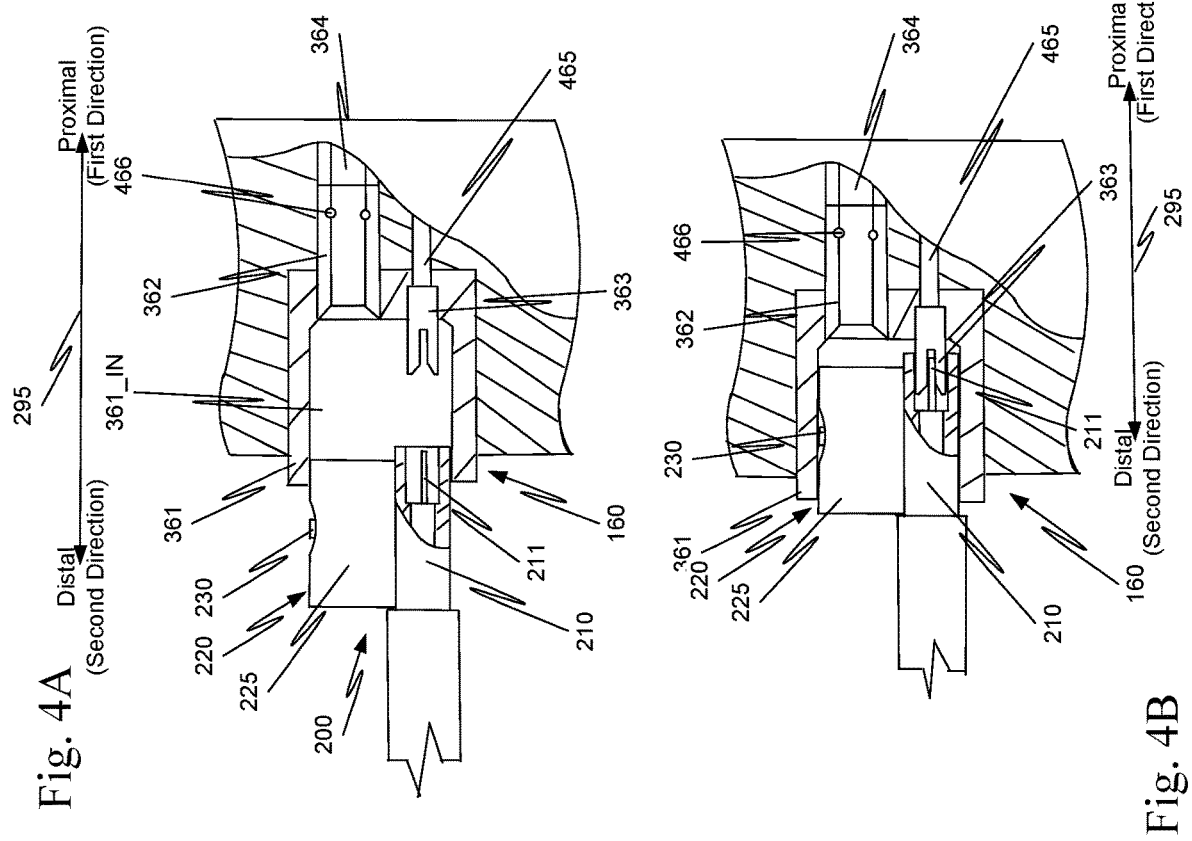
Fig. 5A
Fig. 5B

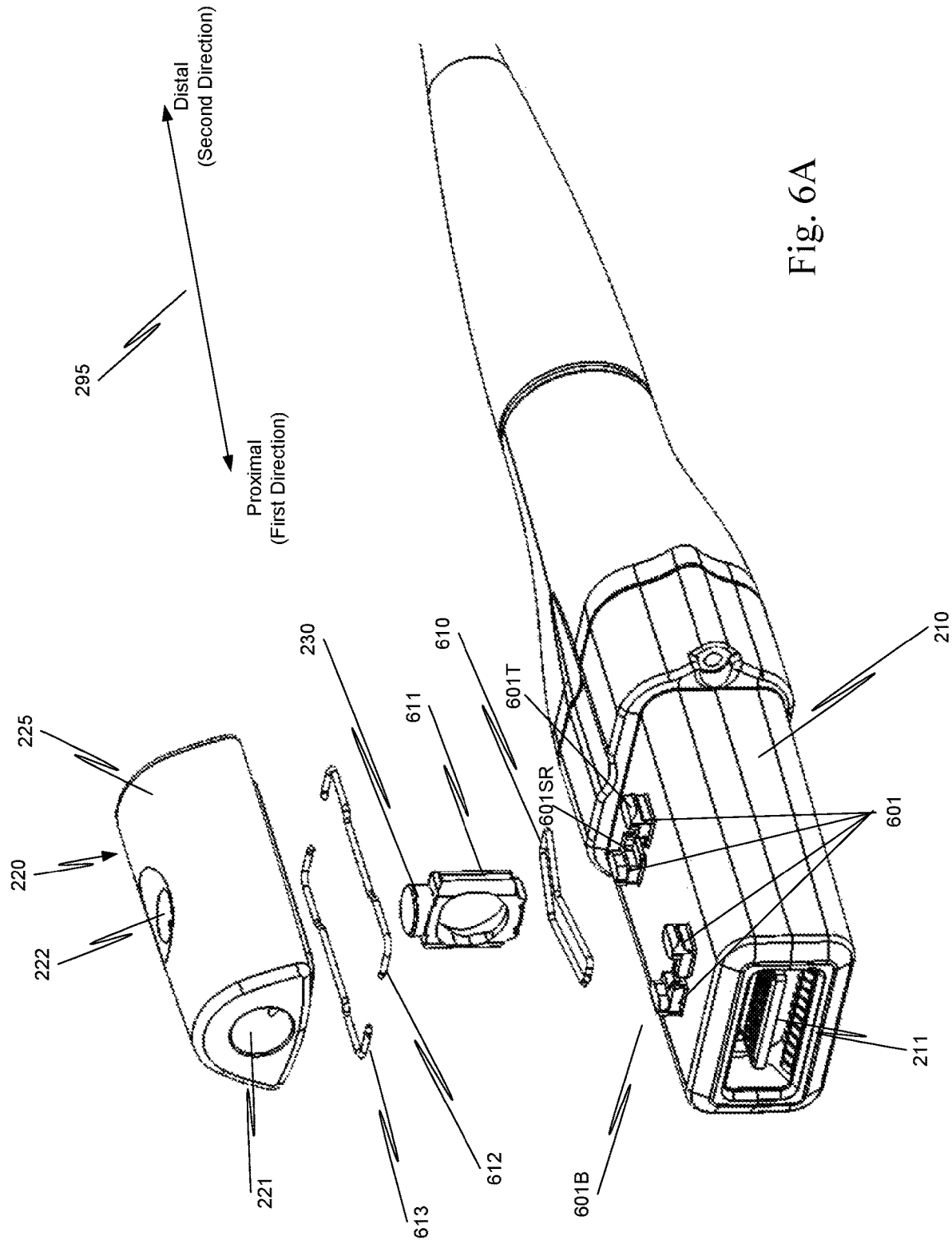

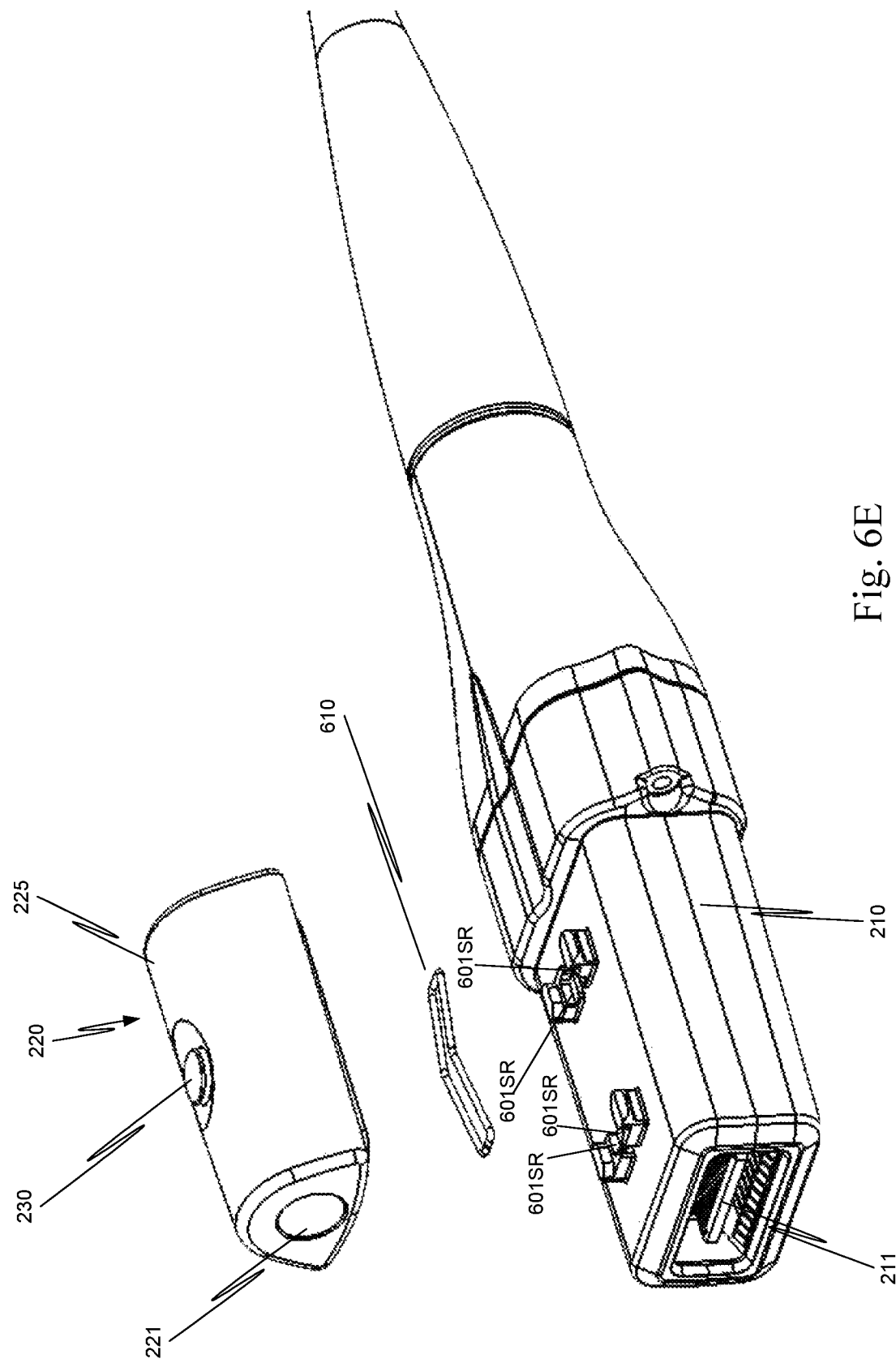

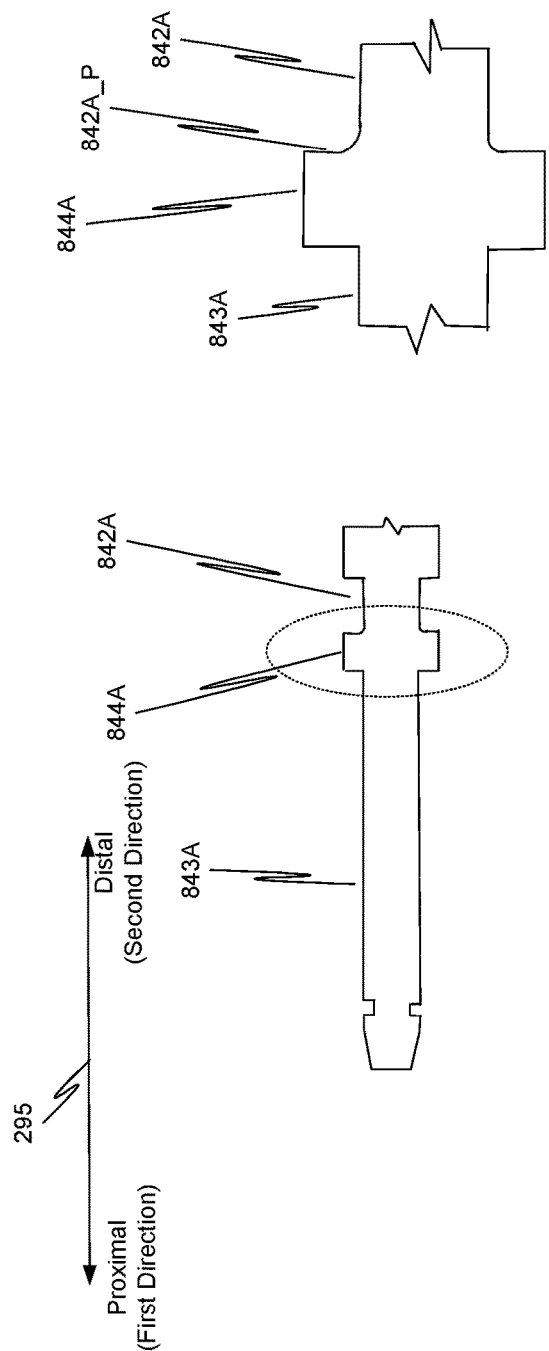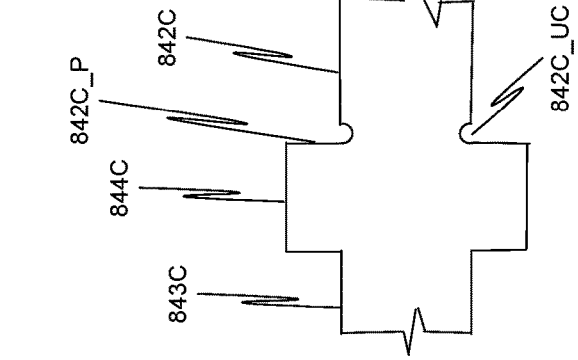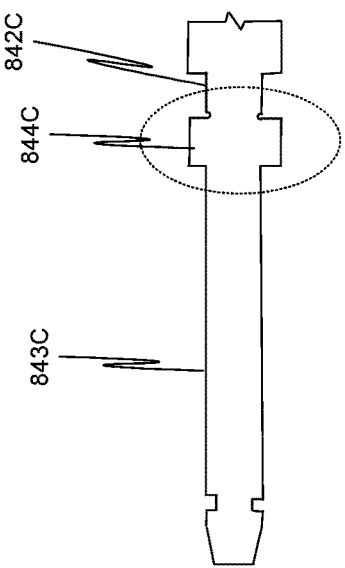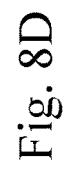

ADAPTER FOR A MULTI-STAGE CONSOLE CONNECTOR

RELATED APPLICATIONS

The present application claims priority to U.S. Provisional Patent Application No. 62/691,453, filed on Jun. 28, 2018, and entitled "An Adapter For A Multi-Stage Console Connector," the contents of which are hereby incorporated by reference in their entirety.

BACKGROUND

Field of the Invention

The present invention relates generally to a medical instrument, and more particularly to an instrument connector of the medical instrument.

Description of Related Art

FIG. 1 illustrates a prior art surgical system 100. Surgical system 100 generally includes a control console 110 coupled to an endoscope 140, a user interface 120, and a display 130. Commands from a clinician input via user interface 120 are used by control console 110 to operate/monitor endoscope 140.

Typically, endoscope 140 is mounted in a patient side support system and is coupled to an instrument manipulator that moves the endoscope 140 in response to commands from control console 110. Endoscope 140 includes an optical channel and power/data channel. In one aspect, endoscope 140 provides illumination to the surgical site and video data to control console 110 that is in turn presented on display 130.

Endoscope 140 includes an instrument connector 150 that mates with a console connector 160 on control console 110 to provide coupling between endoscope 140 and control console 110. Instrument connector 150 and console connector 160 can be disengaged to disconnect endoscope 140 from control console 110.

Instrument connector 150 is an integrated connector that includes both an optical connector and an electrical/data connector that mate with corresponding features in console connector 160 of control console 110. One example of such an instrument connector is described in U.S. Patent Application Publication No. US 2017/0181604 A1 (filed Mar. 17, 2015, disclosing "Multi-stage Instrument Connector").

While console connector 160 works well with an instrument that includes an integrated instrument connector 150, console connector 160 is not suitable for connecting, for example, an endoscope that uses an optical connection and a separate electrical/data connection. Since endoscope 140 is designed for use with a patient side support system, the length of the shaft of endoscope 140 makes endoscope 140 somewhat unwieldly for hand help operation. If in the initial stages of a procedure, it is desired to use a hand held endoscope with separate optical and data/power connectors, it currently requires use of a separate control console, because console connector 160 is not configured to accept separate optical and data/power cables.

SUMMARY

A medical device includes an instrument connector. The instrument connector includes a main body and a coupler fixedly attached to the main body. The main body includes a first interface for a first operational channel for the medical device. The coupler is configured to receive a portion of a cable assembly including a second interface for a second operational channel for the medical device.

In one aspect, the medical device includes the cable assembly including the second interface. The coupler also includes a locking mechanism. Upon passing the portion of the cable assembly through the coupler, the locking mechanism engages the cable assembly, and so the instrument connector includes the first interface for the first operation channel and the second interface for the second operation channel. In one aspect, the locking mechanism includes a gate lock.

In a further aspect, the first operational channel includes an electrical pathway, and the second operational channel includes an optical path. The cable assembly includes one or more fiber optic elements, which are configured to convey illumination light.

In one aspect, the main body includes a coupler mounting interface. The coupler includes an interface configured to connect to the coupler mounting interface and a gate lock. The instrument connector also includes a gate lock engagement spring configured to be mounted in the coupler mounting interface.

The coupler includes a through hole opposite a face of the coupler. The gate lock includes a first end and a second end. When the gate lock is mounted in the coupler through the face of the coupler, the first end of the gate lock extends into the through hole and the second end of the gate lock is configured to rest on the gate lock engagement spring.

In yet another aspect, the instrument connector includes a spring-loaded gate lock having an end extending through a through-hole of the coupler. If the portion of the cable assembly is inserted through the coupler, the spring-loaded gate lock fixedly holds the cable assembly in the coupler, and if the end of the gate lock is depressed, the hold on the cable assembly is released to permit withdrawal of the cable assembly from the coupler.

A console connector is configured to mate with the instrument connector. Upon mating the instrument connector with the console connector, the end of the spring-loaded gate lock is within an inner volume of the console connector. Further, the instrument connector is configured to mate with the console connector without the portion of the cable assembly being received by the coupler.

A method of making an instrument connector for a medical device includes inserting a gate lock into in an opening in a face of a coupler of the instrument connector. The instrument connector is configured to receive a portion of a cable assembly including a second interface for a second operational channel for the medical device. The method then inserts a retaining spring in coupler through the face of the coupler. A gate lock engagement spring is inserted in a coupling mounting interface of a main body of the instrument connector. The main body includes a first interface for a first operational channel for the medical device. Finally, the face of the coupler is mounted on the coupling mounting interface of the main body to fixedly attach the coupler to the main body.

Another method includes inserting an instrument connector into a console connector to mate the instrument connector with the console connector. The instrument connector includes a main body, a coupler fixedly attached to the main body, and a spring-loaded gate lock having an end extending through a through-hole of the coupler. If a portion of a cable assembly is inserted through the coupler, the spring-loaded gate lock fixedly holds the cable assembly in the coupler, and if the end of the gate lock is depressed, the hold on the cable assembly is released to permit withdrawal of the cable assembly from the coupler. Upon mating the instrument connector with the console connector, the end of the spring-loaded gate lock is within an inner volume of the console connector to prevent depression of the end of the gate lock.

BRIEF DESCRIPTION OF THE DRAWINGS

FIGS. 4A and 4B are partial cut-away drawings illustrating the alignment and mating of the instrument connector of FIG. 2A with the console connector of FIG. 3.

FIGS. 5A and 5B are partial cut-away drawings illustrating the alignment and mating of the instrument connector of FIG. 2B with the console connector of FIG. 3.

FIG. 6A and 6B are exploded views of the components in one aspect of the instrument connector of FIGS. 2A and 2B.

FIGS. 6C to 6F illustrate the assembly the instrument connector of FIGS. 2A and 2B.

FIGS. 8A to 8D illustrate aspects of creating an indented region in the second cable assembly of FIGS. 2A and 2B.

Figure 1:
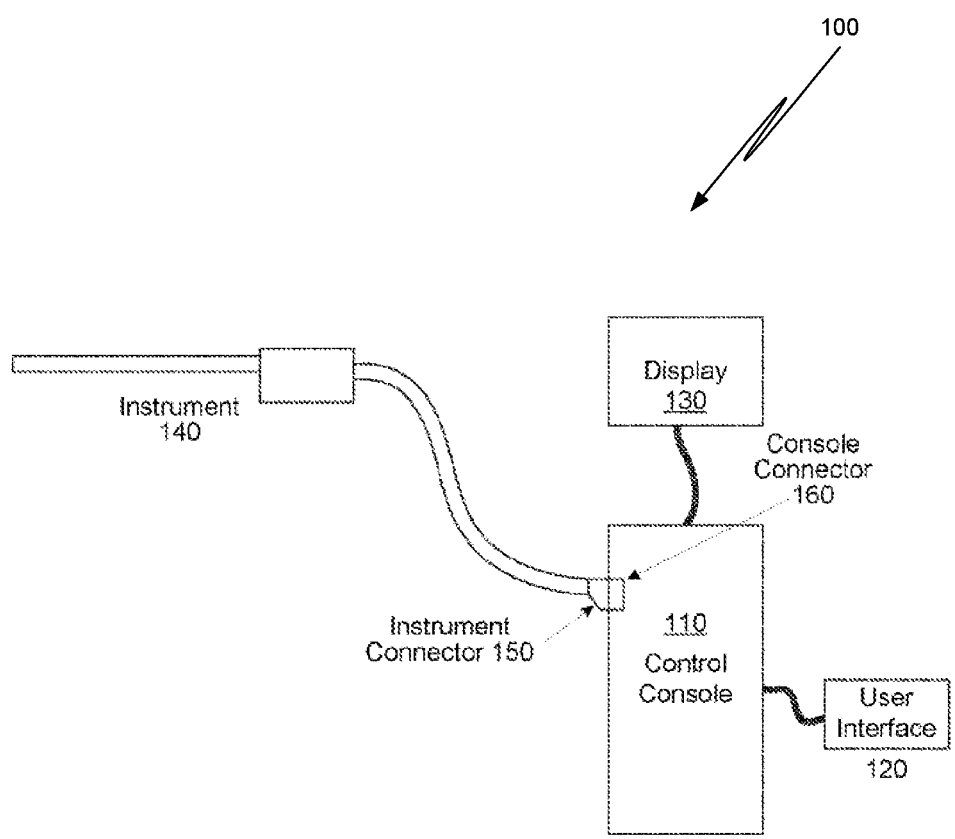
FIG. 1 illustrates a prior art surgical system.

In the drawings, for single digit figure numbers, the first digit in the reference numeral of an element is the number of the figure in which that element first appears. For double-digit figure numbers, the first two digits in the reference numeral of an element are the number of the figure in which that element first appears.

DETAILED DESCRIPTION

A novel connector package 200 (FIG. 2A), sometimes referred to as an instrument connector 200, permits connecting a medical device with two separate discrete interfaces to prior art console connector 160. Herein, two separate discrete interfaces means that the medical device has two different interfaces that are not included in a common connector, and so normally require a console with a separate connector for each of the two different interfaces.

With a medical device that includes instrument connector 200 attached to one of the separate discrete interfaces, a separate console is not required to use the medical device. Instead, control console 110 can be used, for example, initially with a medical device with two separate discrete interfaces and then subsequently with endoscope 140. This streamlines the medical procedure and frees up space that would have been used by separate consoles in the past.

Instrument connector 200 of a medical device includes a main body 210 and a coupler 220 fixedly attached to main body 210. Main body 210 includes a first interface 211 for a first operational channel for the medical device. Main body 210 is connected to a first cable assembly 250 that in turn is connected to components of the medical device.

Coupler 220 is configured to receive a portion of a second cable assembly 240 including a second interface 241 for a second operational channel for the medical device. Coupler 220 includes an open channel 221—a longitudinal open channel—along a lengthwise axis 229 of coupler 220. Coupler 220 includes a second open channel 222 extending from an outer surface of a coupler body 225 in a direction perpendicular to lengthwise axis 229. A locking mechanism release button 230 is positioned in second open channel 222.

Second cable assembly 240 is also connected to components of the medical device. Herein, when it is stated that a cable assembly is connected to components, one knowledgeable in the field understands that one or more parts of the cable assembly, e.g., wires or optic fibers, are connected to the components.

Second cable assembly 240 includes an indented region 242 that starts a predetermined distance from the proximal end of second cable assembly 240. (Arrow 295 defines the proximal direction (a first direction) and the distal direction (a second direction)). As tip 243 of second cable assembly 240, e.g., a portion of second cable assembly 240, is passed through open channel 221 of coupler 220, a locking mechanism engages indented region 242 so that first interface and second interface are fixedly secured in instrument connector 200, and so that instrument connector 200 can be mated with console connector 160. See FIG. 2B. The predetermined distance is determined by a combination of the features of coupler 220, as described more completely below, and the configuration of console connector 160 with which instrument connector 200 is mated.

The locking mechanism prevents the withdrawal of second cable assembly 240 from coupler 220 unless locking mechanism release button 230 is depressed, i.e., activated. As described more completely below, when instrument connector 200 is mated with console connector 160, locking mechanism release button 230 is not accessible, and so cannot be depressed. Consequently, second cable assembly 240 cannot be removed from instrument connector 200 so long as instrument connector 200 is mated with console connector 160.

Figure 3:
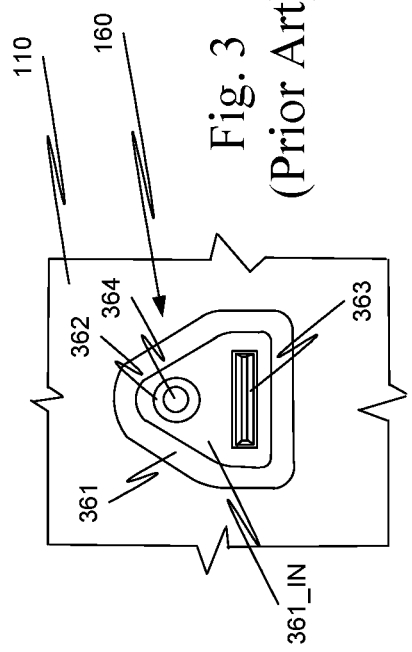
FIG. 3 is an end view of a prior art console connector.

FIG. 3 is an end view of console connector 160 in control console 110. Console connector 160 includes a connector housing 361 that in turn includes a second engagement feature 362 and a first engagement feature 363. Second engagement feature 362 is connected to a second operational channel 364, while first engagement feature 363 is connected to a first operational channel 465. (See FIG. 4A.) Second engagement feature 362 and first engagement feature 363 are included within a volume 361_IN, sometimes referred to as an interior volume, which is bounded by the walls of connector housing 361.

Second engagement feature 362, in this example, includes an optional engagement lock 466 (See FIG. 4A) for establishing a fully connected condition. While depicted as a compliant ridge (e.g., coil spring, O-ring, spring-loaded ball), in various other embodiments, engagement lock 466 can take any form (e.g., clamp, latch, hook, etc.) and can be active as shown or passive (e.g., groove(s), slot(s), etc.), and can be automatically or manually engaged and/or released.

In this example of console connector 160, second engagement feature 362 is depicted as a single cylindrical socket. In various other embodiments, second engagement feature 362 can have any shape (e.g., non-circular socket, tapered socket, prismatic socket, socket with or without additional interior elements, mating pins, etc.) any quantity (e.g., multiple sockets/pins or other features).

Similarly, in this example of console connector 160, first engagement feature 363 is depicted as a rectangular protruding slot. In various other embodiments, first engagement feature 363 can take any form (e.g., empty slot, socket, pins, etc.) and quantity. In addition, in this example, connector housing 361 is an axially asymmetrical shape (pentagon). In various other embodiments, connector housing 361 can take any shape (e.g., circular, square, rectangular, triangular, oval, etc.).

The shape of main body 210, the shape of coupler 220, the configuration of first interface 211, and the configuration of second interface 241 are selected based on the configuration of connector housing 361, second engagement feature 362 and first engagement feature 363 of console connector 160. Thus, the shapes and interfaces illustrated are optional and may be changed to be compatible with a console connector of interest that includes a connector housing including a first engagement feature and a second engagement feature for different operational channels. Herein, an example of the first operational channel is a data/power channel and an example of the second operational channel is an optical channel.

Instrument connector 200 is designed so that instrument connector 200 can be successfully mated with console connector 160 with or without second cable assembly 240 secured in coupler 220. FIGS. 4A and 4B are illustrations of mating instrument connector 200 with console connector 160 without second cable assembly 240 secured in coupler 220. FIGS. 5A and 5B are illustrations of mating instrument connector 200 with console connector 160 with second cable assembly 240 secured in coupler 220.

Figure 2A:
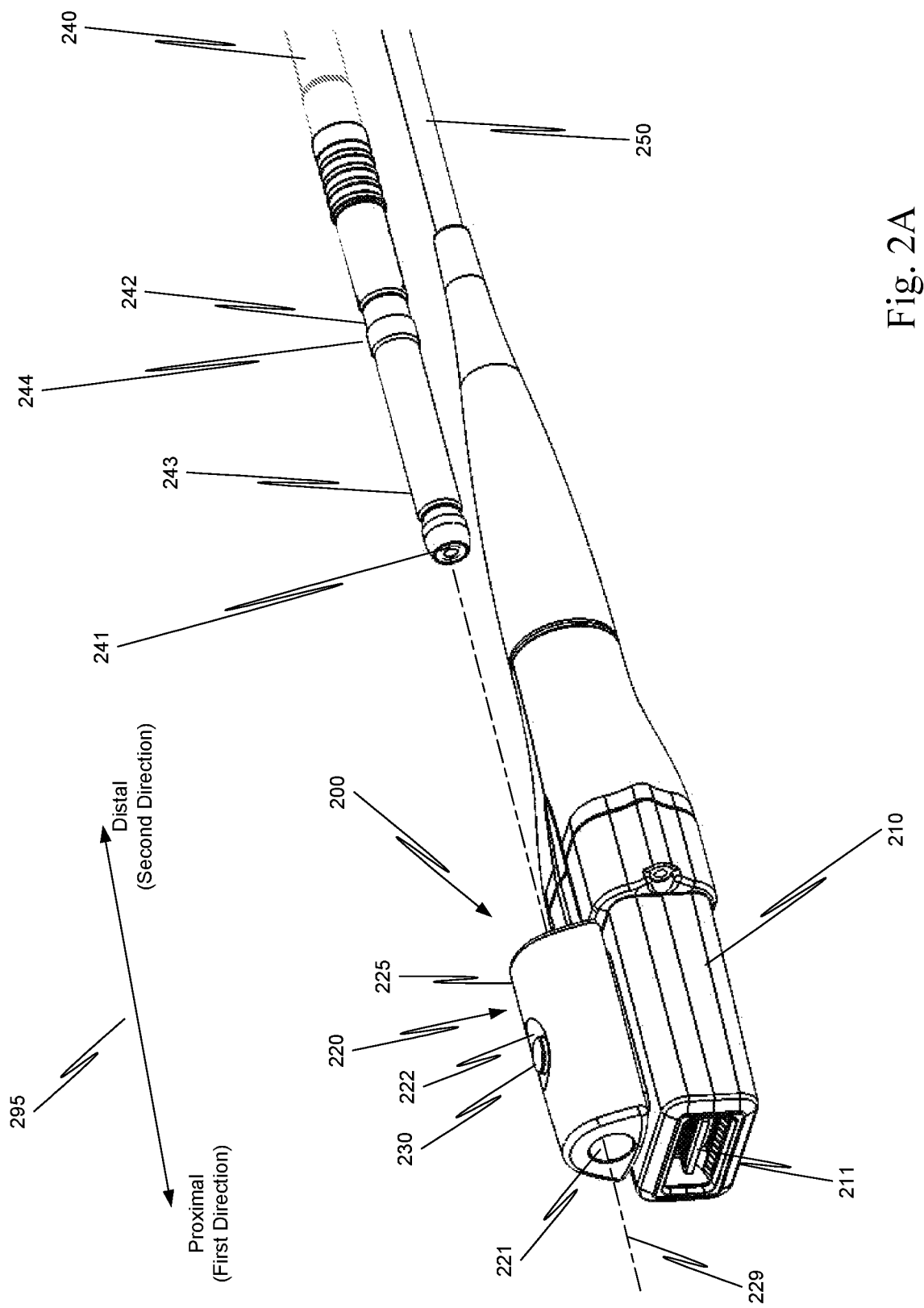
FIG. 2A illustrates an instrument connector mounted on a first cable assembly without a second cable assembly inserted in a coupler of the instrument connector.

FIGS. 4A and 4B are partial cut-away drawings illustrating the alignment and mating of instrument connector 200 (configured as illustrated in FIG. 2A) with console connector 160. In FIG. 4A, instrument connector 200 is being inserted in console connector 160 without second cable assembly 240 being secured in coupler 220. Even though tip 243 of second cable assembly 240 does not extend from coupler 220, the shapes of coupler body 225 and main body 210 establish the correct initial relative positioning between instrument connector 150 and console connector 160. The lengthwise axially asymmetrical shapes of the bodies of instrument connector 200 and console connector 160 enforce a proper rotational orientation and alignment of instrument connector 200 with respect to console connector 160.

As instrument connector 200 is moved further into volume 361_IN, first interface 211 begins to engage with first engagement feature 363 of console connector 160. First interface 211 of instrument connector 200 and first engagement feature 363 can include chamfers, tapers, or any other features to assist in alignment as the features begin to interact with each other. Full engagement of instrument connector 200 and console connector 160 is shown in FIG. 4B.

After instrument connector 200 and console connector 160 are mated, or at any time during the mating process, tip 243 of second cable assembly 240 can be passed through open channel 221 of coupler 220. When tip 243 is passed through coupler 220, the locking mechanism of coupler 220 engages indented region 242 of second cable assembly 240. However, as instrument connector 200 is inserted in console connector 160, locking mechanism release button 230 is located within volume 361_IN of console connector 160, which is bounded by the walls of connector housing 361. Consequently, after tip 243 is passed through coupler 220 and engaged by the locking mechanism of coupler 220, second cable assembly 240 cannot be removed from coupler 220, because locking mechanism release button 230 cannot be depressed until instrument connector 200 is disengaged from console connector 260 and locking mechanism release button 230 is no longer within the walls of connector housing 361.

Figure 2B:
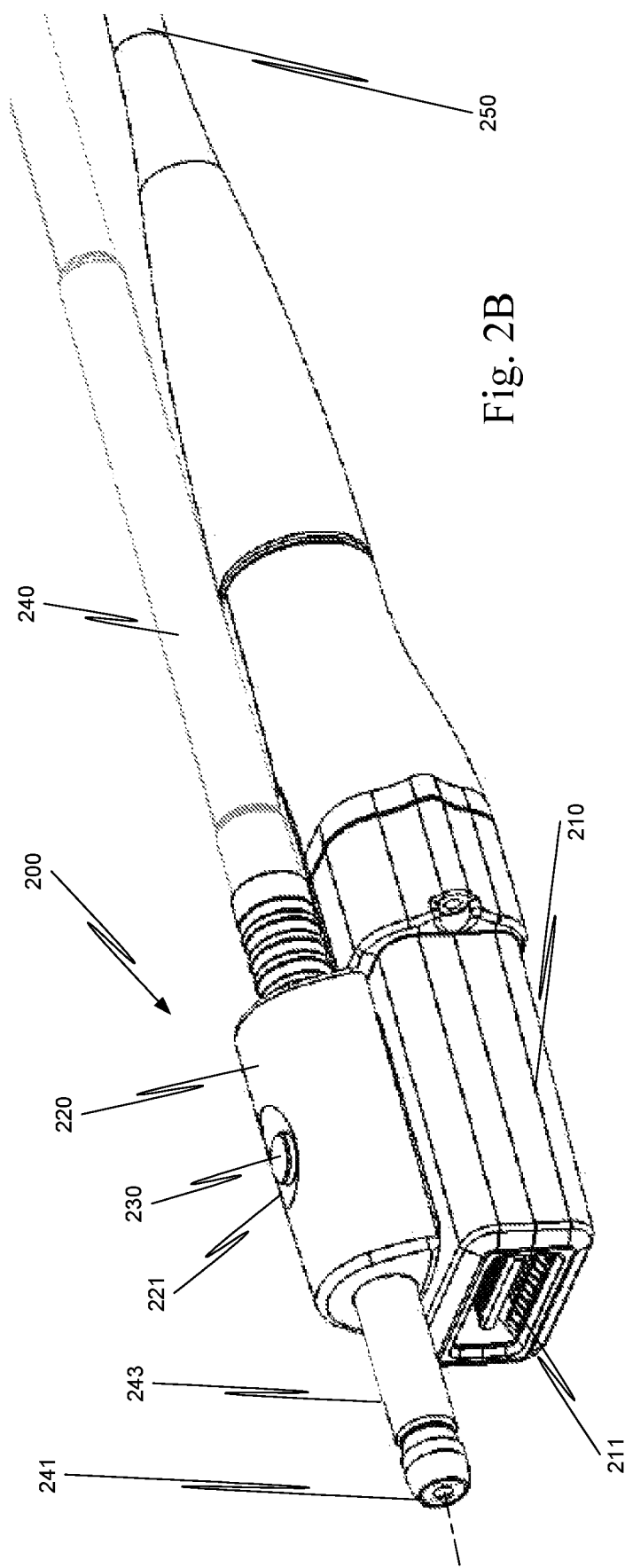
FIG. 2B illustrates the instrument connector of FIG. 2A with a portion of the second cable assembly inserted in the coupler of the instrument connector.

FIGS. 5A and 5B are partial cut-away drawings illustrating the alignment and mating of instrument connector 200 (configured as illustrated in FIG. 2B) with console connector 160. In FIG. 5A, instrument connector 200 is being inserted into console connector 160. Second cable assembly 240 has been secured in coupler 220, before instrument connector 200 is inserted into console connector 160. Thus, in this aspect, in addition to the shapes of coupler body 225 and main body 210 that assist in aligning first interface 211 of instrument connector 200 with first engagement feature 363 of console connector 160, tip 243 is available to assist in establishing the proper alignment.

As instrument connector 200 is moved further into volume 361_IN, second interface 241 enters second engagement feature 362 of console connector 160 before first interface 211 begins to engage with first engagement feature 363 of console connector 160. Establishing an accurate alignment of instrument connector 200 with console connector 160 using a combination of tip 243 and second engagement feature 362 as well as the shapes of instrument connector 200 and connector housing 361 of console connector 160 ensures that first interface 211 and first engagement feature 363 can be accurately engaged with minimal risk of damage. This is particularly beneficial where first interface 211 and/or first engagement feature 363 are delicate or difficult/costly to replace (e.g., electrical connectors for imaging or sensor data transmission).

Again, as instrument connector 200 is inserted in console connector 160, locking mechanism release button 230 is located within volume 361_IN of console connector 160, which is bounded by the walls of connector housing 361. Consequently, second cable assembly 240 cannot be removed from coupler 220, because locking mechanism release button 230 cannot be depressed until instrument connector 200 is disengaged from console connector 260 and locking mechanism release button 230 is no longer within the walls of connector housing 361.

Figure 6B:
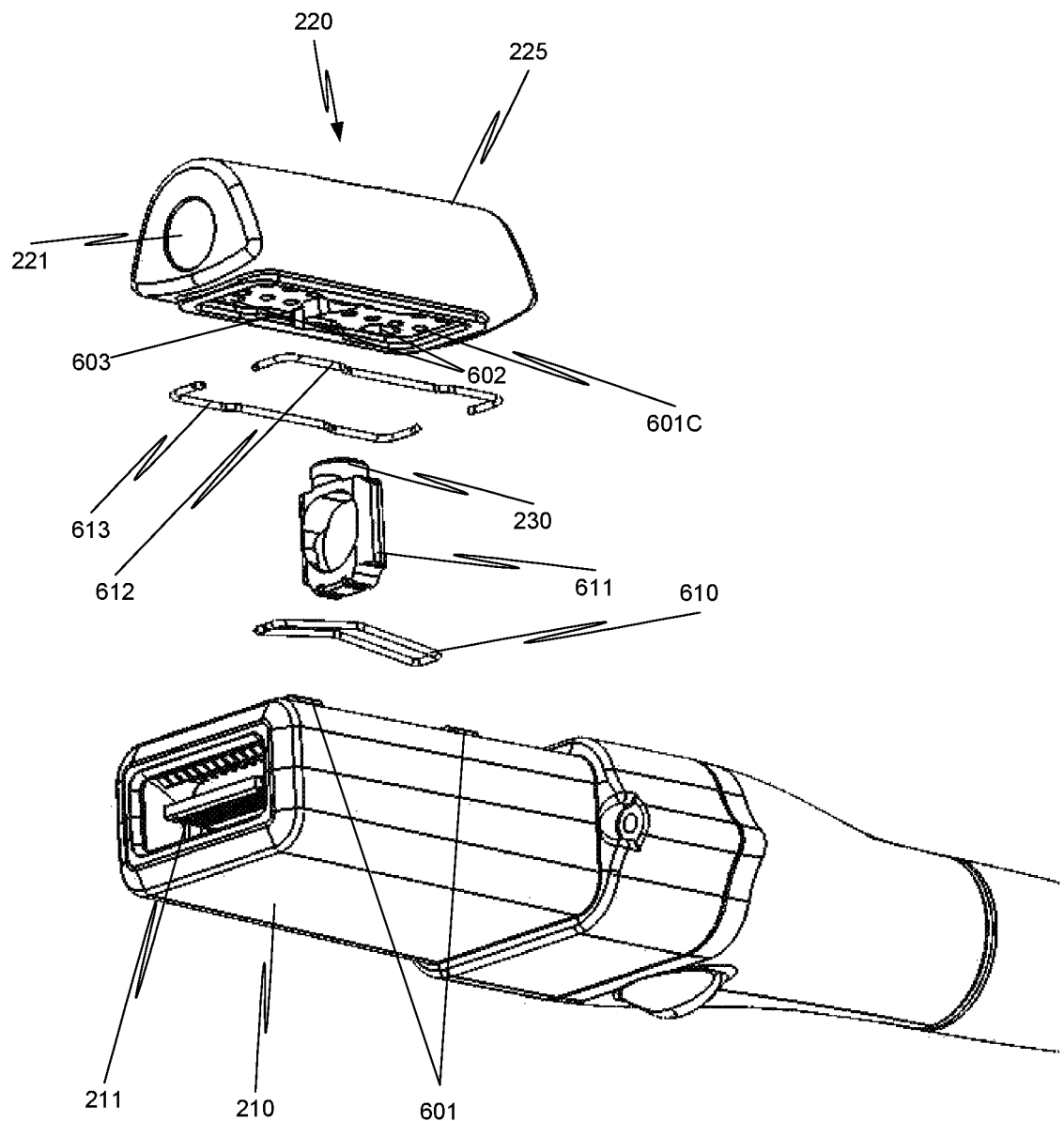

FIG. 6A and 6B are exploded views of the components in one aspect of instrument connector 200. In addition to main body 210 and coupler body 225, instrument connector 200 includes retaining springs 612, 613, a gate lock 611 that includes an end configured as locking mechanism release button 230, and a gate lock engagement spring 610. The combination of gate lock engagement spring 610 and gate lock 611, when mounted in instrument connector 200, are an example of a locking mechanism.

Also, in this aspect, a face of main body 210 includes a coupler connector interface 601B. Coupler connector interface 601B includes a plurality of three-dimensional spring support and tab connecting elements 601 extending from a face of main body 210. Each of plurality of three-dimensional spring support and tab connecting elements 601 includes a spring support and retainer element 601SR on a first side and on a second side, a tab connector 601T, where the first side is opposite to the second side. In this example, spring support and retainer element 601SR is on an inner side of the three-dimensional spring support and tab connecting element, and tab connector 601T is on an outer side of the three-dimensional spring support and tab connecting element. Retaining springs 612, 613 also interact with tab connector 601T to secure coupler body 225 to main body 210.

A face of coupler body 225 includes a body mounting interface 601C (FIG. 6B). Body mounting interface 601C includes a plurality of receiving elements 602—one for each of plurality of three-dimensional spring support and tab connecting elements 601. Body mounting interface 601C also includes a first groove 1002 (FIG. 10) for first retaining spring 612 and a second groove 1003 for second retaining spring 613. Each of plurality of receiving elements 602 is configured so that a corresponding three-dimensional spring support and tab connecting element can pass through the receiving element and tab connector 601T engage a surface within coupler body 225. Body mounting interface 601C also includes a slot 603 configured to receive gate lock 611.

Figure 6C:
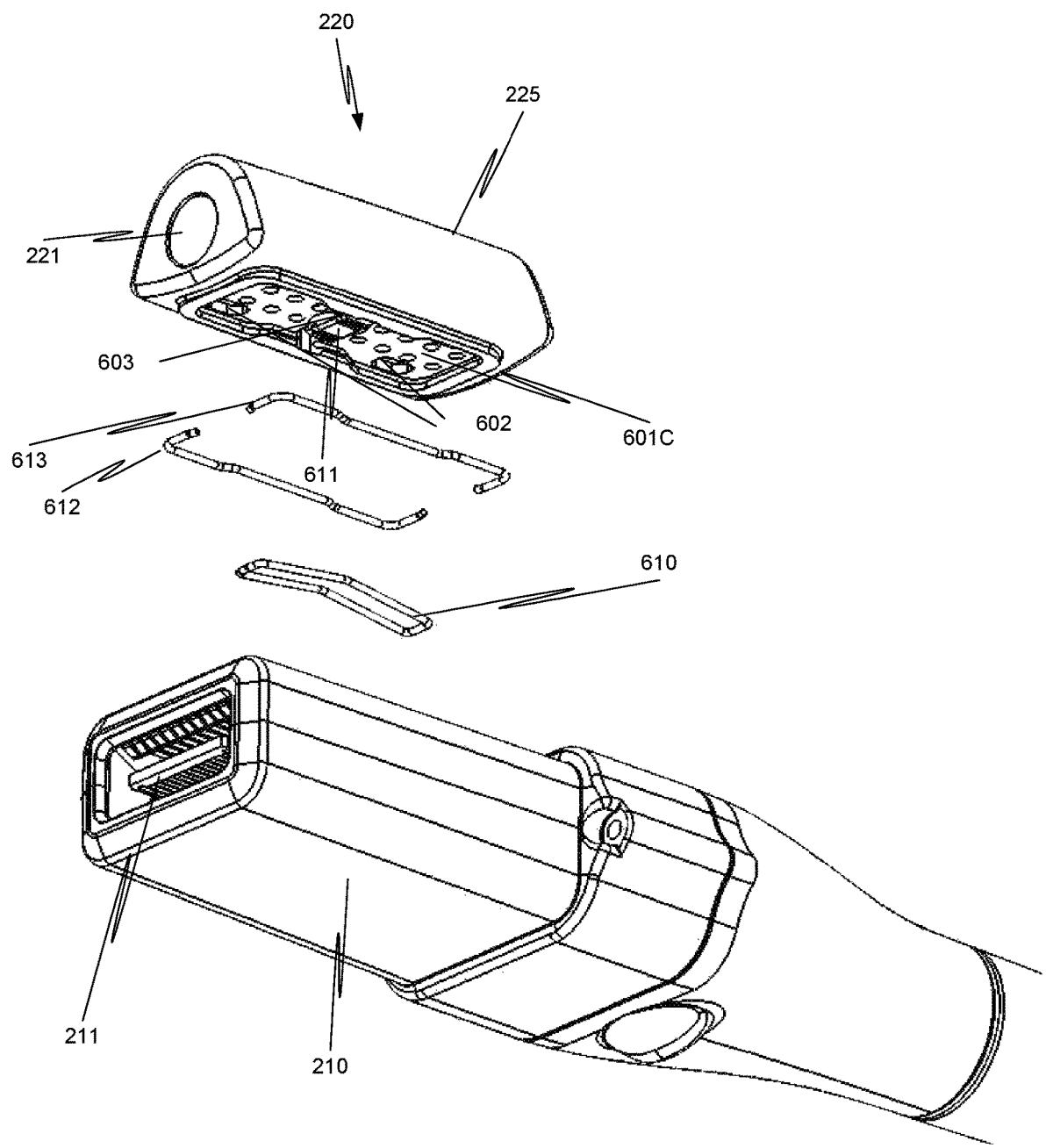
Figure 6D:
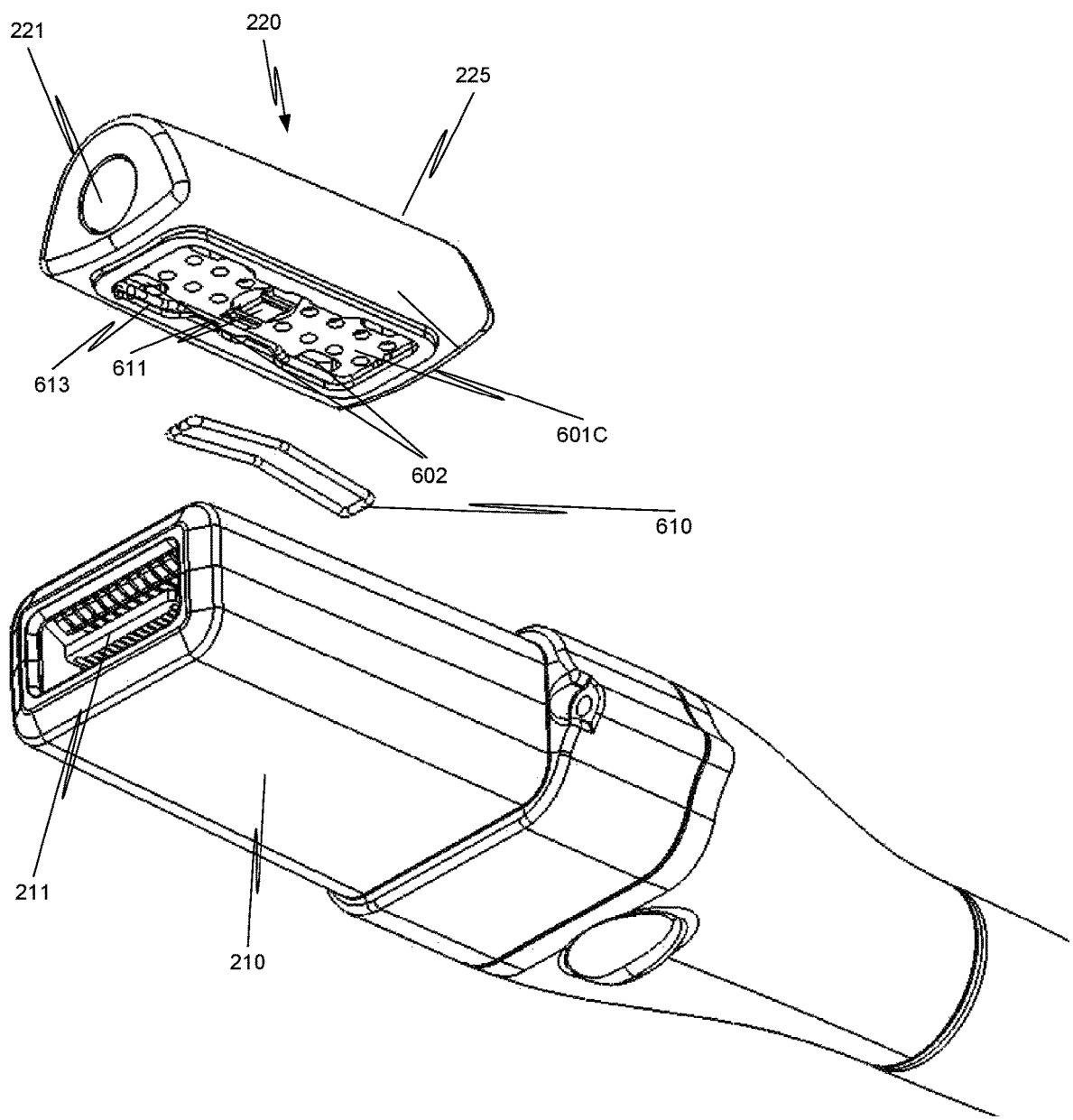

In FIG. 6C, gate lock 611 is inserted into slot 603. In FIG. 6D, each of retaining springs 612, 613 has been placed in a corresponding groove 1002, 1003 (See FIG. 10) in body mounting interface 601C. In this aspect, two retaining springs 612, 613 are used to facilitate manufacturing of the springs. However, in another aspect, the retaining springs can be one unified spring.

Figure 6F:
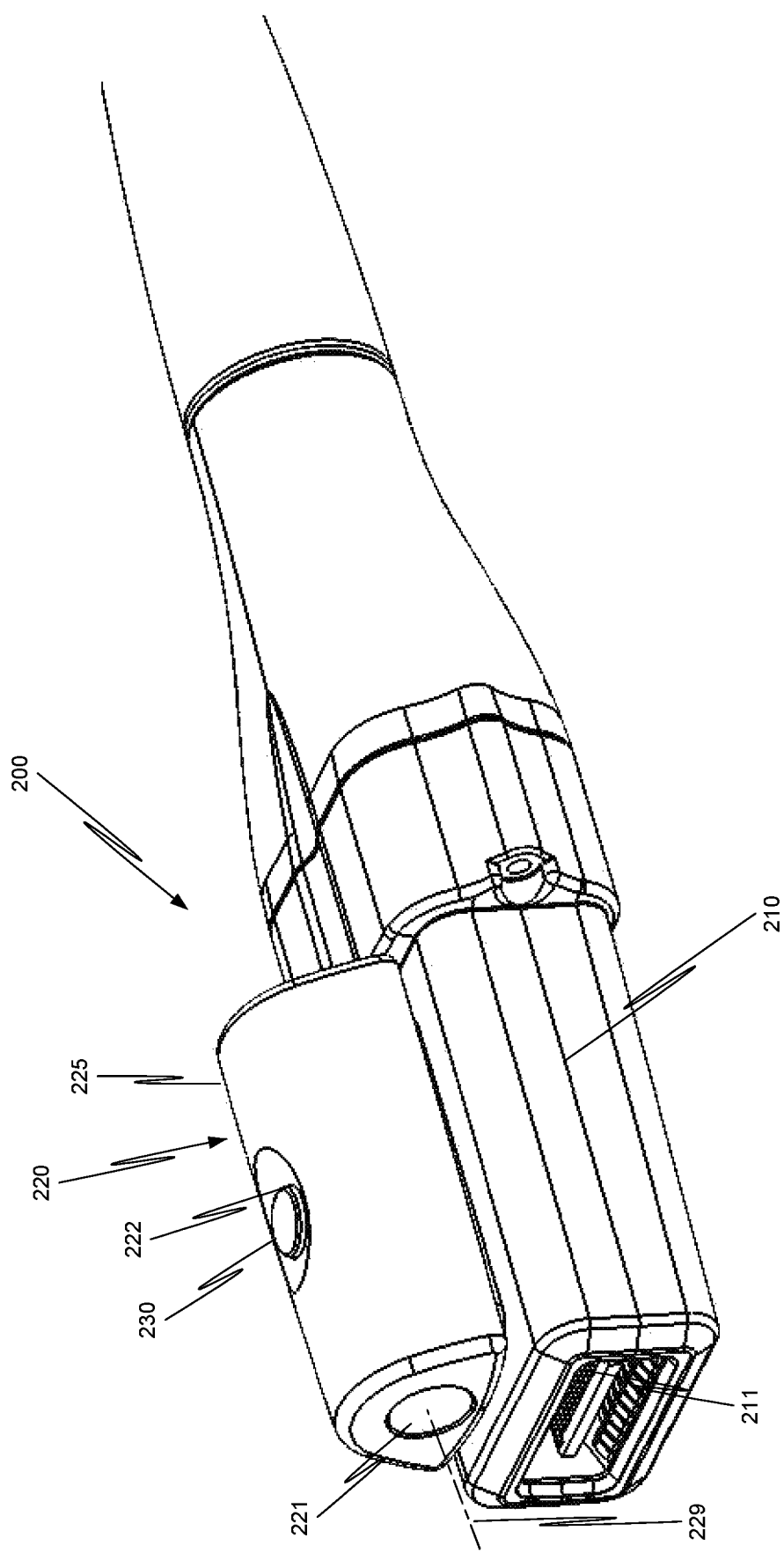

In FIG. 6E, gate lock engagement spring 610 is aligned with spring support and retainer elements 601SR and mounted in the receptacle formed by spring support and retainer elements 601SR. Each of plurality of receiving elements 602 is aligned with a corresponding one of plurality of three-dimensional spring support and tab connecting elements 601, and then coupler 220 is snapped into place on main body 210, which results in instrument connector 200, as illustrated in FIG. 6F.

Figure 7:
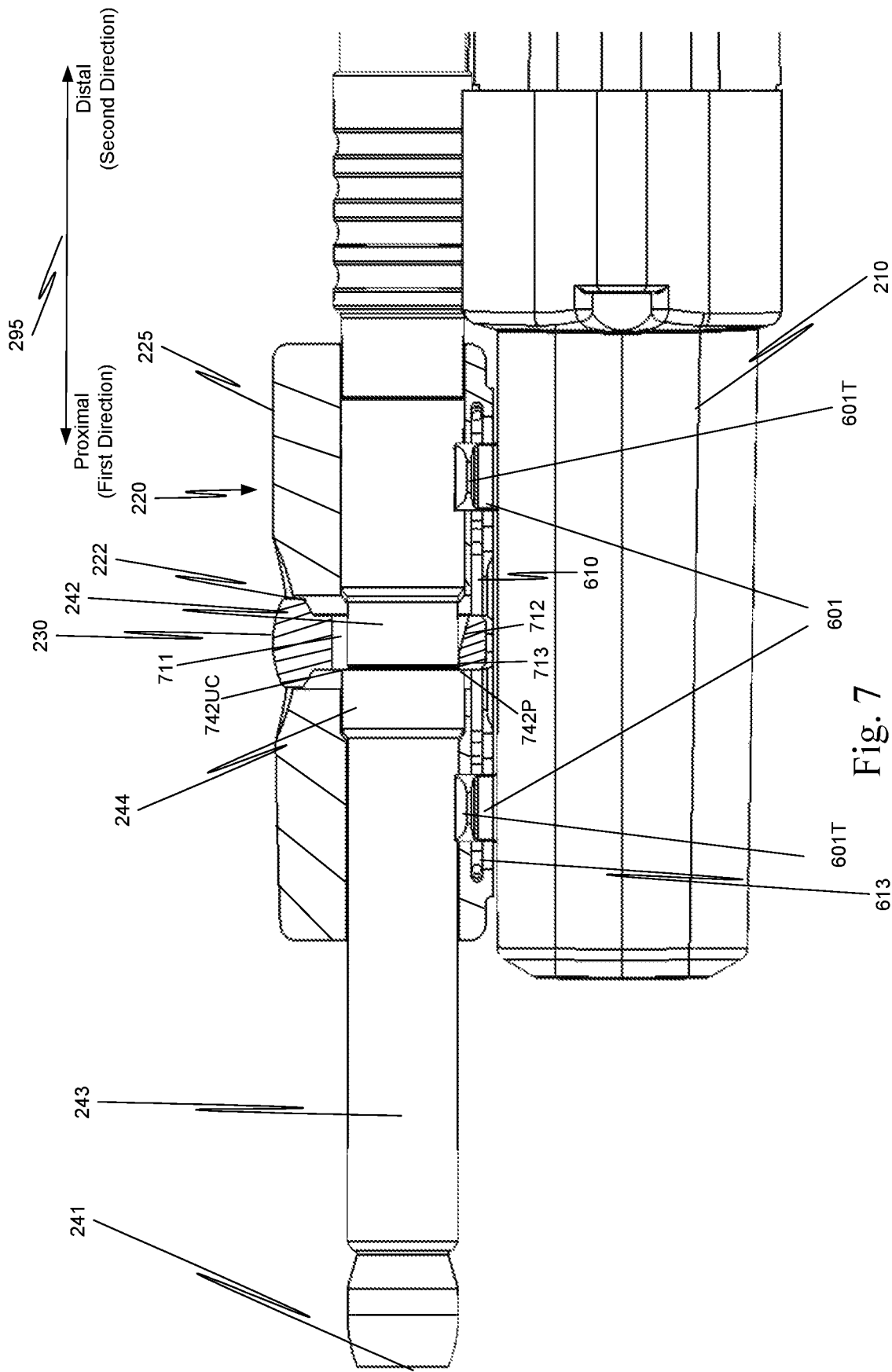
FIG. 7 is a cutaway view along the lengthwise axis of the coupler of FIGS. 2A and 2B.

FIG. 7 is a cutaway view along the lengthwise axis of coupler 220. A tip 243 of second cable assembly 240 is passed through a through opening 711 in gate lock 611. A tapered surface 712 of through opening 711 guides tip 243 over a locking lip portion 713 that bounds a portion of through opening 711. As larger diameter region 244 of second cable assembly 240 passes over locking lip portion 713, gate lock 611 is pushed down, e.g., is pushed in a direction towards main body 210.

As soon as the leading edge, a proximal edge, of indented region 242 passes over a proximal edge of locking lip portion of gate lock 611, gate lock engagement spring 610 pushes gate lock 611 in an upward direction, e.g., in a direction away from main body 210, until locking lip portion 713 contacts an outer circumferential surface of indented region 242. When locking lip portion 713 is in indented region 242, second cable assembly 240 can be moved in the axial direction along an axial length of indented region 242, but second cable assembly 240 cannot be removed from coupler 220 because a proximal edge surface 742P of indented region 242 contacts a proximal edge surface of locking lip portion 713. Thus, second cable assembly 240 is fixedly attached to coupler 220. When locking mechanism release button 230 is depressed, gate lock 611 is moved down so that locking lip portion 713 is no long in indented region 242, and so second cable assembly 240 can be moved axially in the distal direction to remove tip 243 from coupler 220.

In one aspect, proximal end 742UC of the outer circumferential surface of indented region 742 is optionally undercut to provide a more positive lock between locking lip portion 713 of gate lock 611 and proximal edge surface 742P of indented region 242. When a radial length of proximal edge surface 742P is small, e.g., 0.5 mm, the increase of the radial length of proximal edge surface 742P improves the gripping capability of locking lip portion 713, i.e., the gripping capability of gate lock 611.

The advantage of the undercut is demonstrated in FIGS. 8A to 8D. FIGS. 8A and 8C are illustrations of tips 843A, 843B, larger diameter regions 844A, 884C, and indented regions 842A, 842C of cable assemblies that can be inserted in coupler 220. FIG. 8B is an enlarged diagram of the region included in the dotted circle of FIG. 8A, while FIG. 8D is an enlarged diagram of the region included in the dotted circle of FIG. 8C.

In FIGS. 8A and 8B, indented region 842A is formed in larger diameter region 844A using conventional machining. The shape of the tool used in the machining results in a curved region in the transition from proximal side wall 842A_P to the outer circumferential surface of indented region 842A. This curved region reduces the straight wall portion of proximal side wall 842A_P.

In FIGS. 8C and 8D, indented region 842C is formed in larger diameter region 844A using conventional machining. The shape of the tool used in the machining results in a curved region in the transition from proximal side wall 842C_P to the outer circumferential surface of indented region 842C. However, this curved region is removed by undercutting the outer circumferential surface of indented region 842C that is adjacent to proximal side wall 842C_P to form undercut region 842C_UC. Undercut region 842C_UC makes the whole radial length of the proximal side wall 842A_P from the outer circumferential surface of larger diameter region 844C to the outer circumferential surface of indented region 842C available.

If the radial length of the proximal side wall of the indented region is such that gate lock 611 can securely hold a cable assembly in coupler 220, the tip of FIG. 8A can be used, but as the radial length of the proximal side wall of the indented region becomes around 0.5 mm, the increased length provided by the undercut allows gate lock 611 to provide a more secure grip on the cable tip relative to the configuration of FIG. 8A. This, in turn, helps assure that the cable assembly cannot be inadvertently removed from coupler 220.

Figure 9:
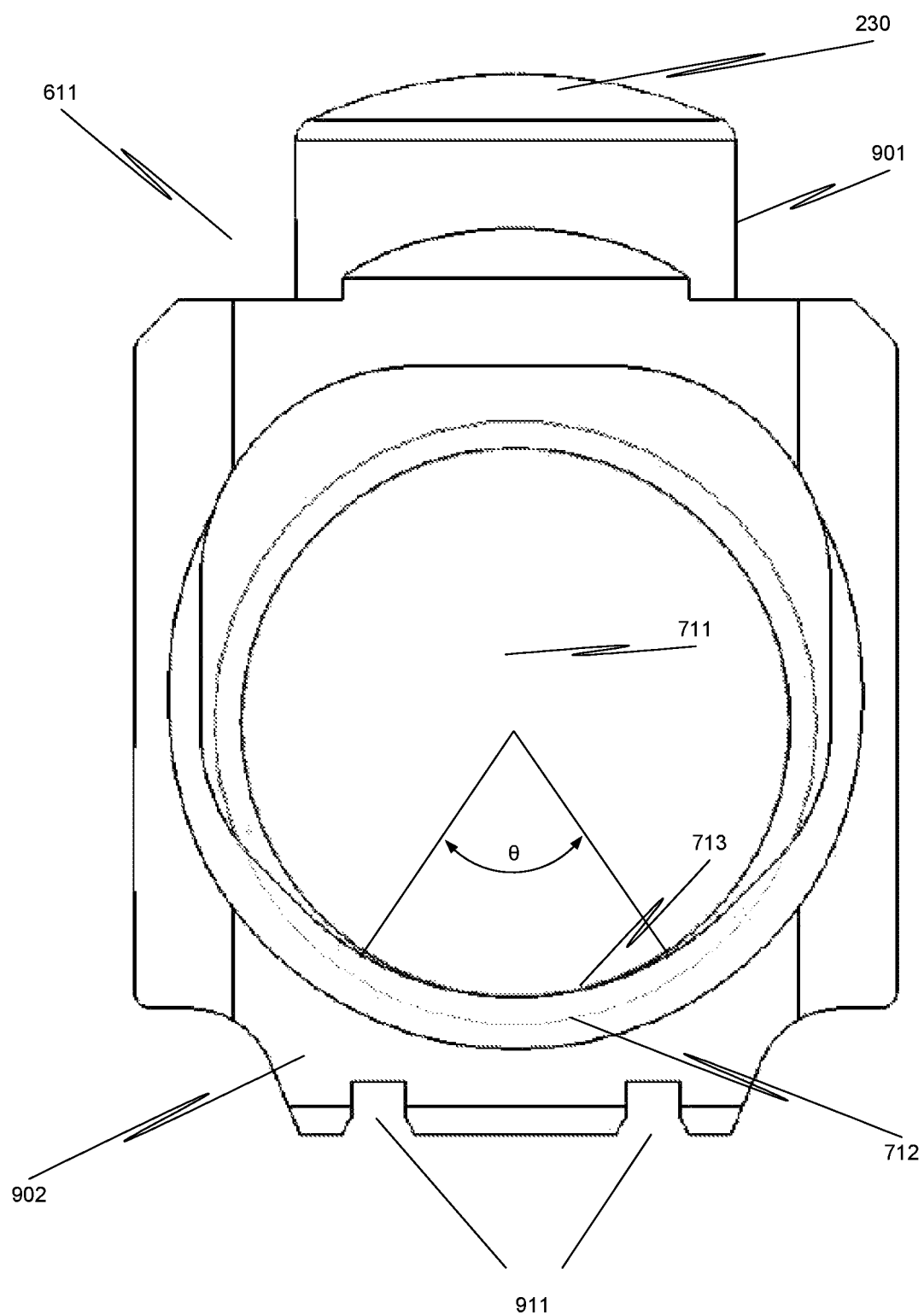
FIG. 9 is an illustration of one aspect of a gate lock, looking axially in the proximal direction, of the coupler in FIGS. 2A and 2B.

FIG. 9 is an illustration of one aspect of gate lock 611 looking axially in the proximal direction of FIG. 2A. Gate lock 611 includes a first end 901 and a second end 902. First end 901 of gate lock 611 is configured to extend into through second open channel 222 in coupler body 225 of coupler 220 and second end 902 of the gate lock 611 is configured to rest on gate lock engagement spring 610. Through opening 711 is positioned between first end 901 and second end 902 with locking lip portion 713 adjacent to second end 902.

First end 901 includes locking mechanism release button 230. Second end 902 includes two notches 911 configured to sit on gate lock engagement spring 610. Gate lock 611, in this aspect, has a wrap angle $\theta$ that provides contact between locking lip portion 713 and indented region 242 of second cable assembly 240. In one aspect, gate lock 611 is configured so that wrap angle $\theta$ provides sixty degree contact with indented region 242 of second cable assembly 240.

Figure 10:
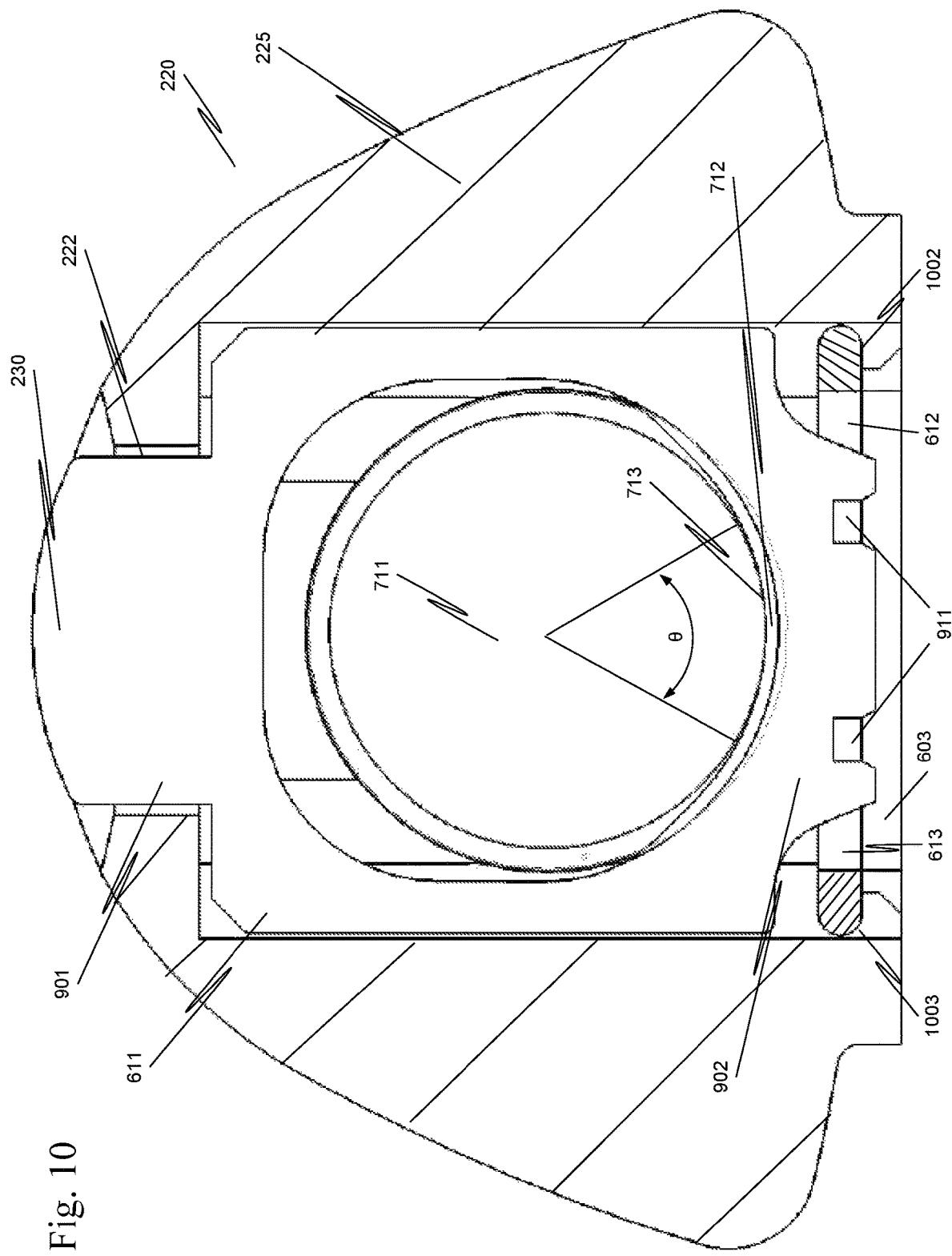
FIG. 10 is a cross-section view (perpendicular to the lengthwise axis) of the configuration of the coupler as illustrated in FIG. 6E.

FIG. 10 is a cross-section view (perpendicular to the lengthwise axis) of the configuration of coupler 220 as illustrated in FIG. 6E. FIG. 10 shows gate lock 611 and retaining springs 612, 613 mounted in coupler body 225 of coupler 220.

As used herein, "first," "second," "third," "fourth," etc. are adjectives used to distinguish between different components or elements. Thus, "first," "second," "third," "fourth," etc. are not intended to imply any ordering of the components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

I claim:

1. A medical device comprising:
an instrument connector configured to be mated with a mating connector, the instrument connector comprising:
a main body including a first interface for a first operational channel for the medical device; and
a coupler fixedly attached to the main body, the coupler forming a longitudinal through hole that is laterally enclosed along a longitudinal axis, the coupler configured to receive a portion of a cable assembly as the portion of the cable assembly is passed along the longitudinal axis into the longitudinal through hole until the portion of the cable assembly reaches and is releasably locked in a locked position, the portion of the cable assembly including a second interface for a second operational channel for the medical device;
the coupler comprising a gate lock configured to releasably lock the portion of the cable assembly in the locked position;
the main body further comprising a coupler mounting interface; and
the instrument connector further comprising a gate lock engagement spring configured to be mounted in the coupler mounting interface.

2. The medical device of claim 1, further comprising:
the cable assembly including the second interface; and
an additional cable assembly attached to the first interface of the main body.

3. The medical device of claim 2:
wherein upon the portion of the cable assembly being passed into the longitudinal through hole, the gate lock engages the portion of the cable assembly in the locked position; and
wherein upon engagement of the portion of the cable assembly by the gate lock, the instrument connector comprises the first interface for the first operational channel and the second interface for the second operational channel, wherein the first interface and the second interface are configured to be mated with the mating connector.

4. The medical device of claim 1, wherein:
the first operational channel comprises an electrical pathway;
the second operational channel comprises an optical channel; and
the cable assembly includes one or more fiber optic elements.

5. The medical device of claim 4, wherein the one or more fiber optic elements are configured to convey illumination light.

6. The medical device of claim 1:
the coupler further comprising an interface configured to connect to the coupler mounting interface.

7. The medical device of claim 1:
the gate lock further comprising a first end and a second end, the first end of the gate lock extending into the longitudinal through hole and the second end of the gate lock being configured to rest on the gate lock engagement spring.

8. A medical device comprising:
an instrument connector configured to be mated with a mating connector, the instrument connector comprising:
a main body including a first interface for a first operational channel for the medical device;
a coupler fixedly attached to the main body, the coupler forming a longitudinal through hole that is laterally enclosed along a longitudinal axis, the coupler configured to receive a portion of a cable assembly as the portion of the cable assembly is passed along the longitudinal axis into the longitudinal through hole until the portion of the cable assembly reaches and is releasably locked in a locked position, the portion of the cable assembly including a second interface for a second operational channel for the medical device; and
a spring-loaded gate lock having an end extending laterally through the longitudinal through hole of the coupler, wherein when the portion of the cable assembly is passed into the longitudinal through hole of the coupler, the spring-loaded gate lock fixedly holds the portion of the cable assembly in the coupler, and wherein if the end of the gate lock is depressed, the hold on the portion of the cable assembly is released to permit withdrawal of the portion of the cable assembly from the longitudinal through hole of the coupler.

9. The medical device of claim 8,
wherein upon mating the instrument connector with the mating connector, the end of the spring-loaded gate lock is within an inner volume of the mating connector.

10. The medical device of claim 1, wherein the instrument connector is configured to mate with the mating connector without the portion of the cable assembly being received by the coupler, and the coupler is configured to receive the portion of the cable assembly into the longitudinal through hole of the coupler while the instrument connector is mated with the mating connector.

11. A medical device comprising:
an instrument connector comprising:
 a main body including a first interface for a first operational channel for the medical device; and
 a coupler fixedly attached to the main body, the coupler configured to receive a portion of a cable assembly including a second interface for a second operational channel for the medical device, the coupler including
  a coupler body forming a longitudinal through hole that is laterally enclosed along a longitudinal axis;
  a locking mechanism configured to engage the cable assembly when the portion of the cable assembly is received in the longitudinal through hole such that the instrument connector positions the first interface and the second interface to be mated with a mating connector, and
  a lock release mechanism configured to be activated to release the locking mechanism to permit withdrawal of the portion of the cable assembly from the longitudinal through hole, wherein the lock release mechanism comprises a button on an end of a gate lock extending into the longitudinal through hole.

12. The medical device of claim 11, wherein upon mating the instrument connector with the mating connector, the lock release mechanism is within an inner volume of the mating connector to prevent activation of the lock release mechanism while the instrument connector is mated with the mating connector.

13. The medical device of claim 11, wherein if the gate lock is depressed, the cable assembly is released to permit withdrawal of the cable assembly from the longitudinal through hole.

14. The medical device of claim 13, wherein upon mating the instrument connector with the mating connector, the gate lock is within an inner volume of the mating connector to prevent the gate lock from being depressed when the instrument connector is mated with the mating connector.

15. The medical device of claim 11, wherein:
the medical device comprises an endoscope; and
the mating connector comprises a console connector of a control console.

\* \* \* \* \*